(12) United States Patent
Yacoubian et al.

(10) Patent No.: US 8,298,169 B2
(45) Date of Patent: Oct. 30, 2012

(54) SYSTEM, METHODS AND APPARATUS FOR CEREBRAL PROTECTION

(76) Inventors: Vahe Stephan Yacoubian, Glendale, CA (US); Hrayr Karnig Shahinian, Pasadena, CA (US)

(*) Notice: Subject to any disclaimer, the term of this patent is extended or adjusted under 35 U.S.C. 154(b) by 1565 days.

(21) Appl. No.: 11/053,622

(22) Filed: Feb. 8, 2005

(65) Prior Publication Data

US 2005/0209579 A1 Sep. 22, 2005

Related U.S. Application Data

(60) Provisional application No. 60/555,221, filed on Mar. 22, 2004.

(51) Int. Cl.
*A61M 1/00* (2006.01)
*A61M 37/00* (2006.01)

(52) U.S. Cl. ........................ 604/28; 604/4.01

(58) Field of Classification Search ............... 604/4.01, 604/6.14, 6.16, 8, 19, 26, 28, 96.01, 98.01, 604/101.04, 102.01–102.03, 104, 500, 506–509, 604/907, 912, 915, 919, 921; 435/1.1, 1.2, 435/2, 283.1; 128/DIG. 12, DIG. 13
See application file for complete search history.

(56) References Cited

U.S. PATENT DOCUMENTS

| | | | | |
|---|---|---|---|---|
| 5,011,468 | A | * | 4/1991 | Lundquist et al. ............. 600/18 |
| 5,794,629 | A | | 8/1998 | Frazee |
| 5,865,789 | A | | 2/1999 | Hattler |
| 5,908,407 | A | | 6/1999 | Frazee et al. |
| 6,110,139 | A | * | 8/2000 | Loubser ........................ 604/30 |
| 6,383,172 | B1 | | 5/2002 | Barbut |
| 6,386,202 | B1 | | 5/2002 | Frazee |
| 6,555,057 | B1 | | 4/2003 | Barbut et al. |
| 6,896,663 | B2 | | 5/2005 | Barbut |
| 2001/0038807 | A1 | * | 11/2001 | Barbut et al. ................. 422/44 |
| 2002/0010411 | A1 | | 1/2002 | Macoviak et al. |
| 2002/0132845 | A1 | | 9/2002 | Miller et al. |
| 2002/0143362 | A1 | | 10/2002 | Macoviak et al. |
| 2003/0023200 | A1 | | 1/2003 | Barbut et al. |
| 2003/0097036 | A1 | | 5/2003 | St. Germain et al. |
| 2003/0158571 | A1 | | 8/2003 | Esch et al. |
| 2003/0158574 | A1 | | 8/2003 | Esch et al. |
| 2003/0191448 | A1 | | 10/2003 | Swindle |
| 2003/0195382 | A1 | | 10/2003 | Barbut |

OTHER PUBLICATIONS

Bartoccioni, Sandro et al. Retrograde cerebral perfusion for aortic operations through left thoracotomy Ann Thorac Surg 1999 67: 1815-1816.*
Calkavur, Tanzer et al. Clinical Results of Retrograde Cerebral Perfusion in Treatment of Aortic Disease Asian Cardiovasc Thorac Ann 1998 6: 288-294.*

* cited by examiner

*Primary Examiner* — Nicholas Lucchesi
*Assistant Examiner* — Nathan R Price

(57) ABSTRACT

A device, system and method for perfusing an oxygenated medium in the cerebral vasculature includes positioning pressure cuffs on upper extremities; providing a catheter having a multi-region configuration with a balloon; inserting the catheter into a subclavian or femoral vein; advancing the catheter such that the balloon is positioned substantially in the superior vena cava junction substantially proximal to the take-off of the left inominate vein. During a perfusion mode, the cuffs and balloon are inflated causing an increase in cerebral blood flow, retrogradely; and oxygenated blood which may be cooled is pumped from a femoral artery into the catheter for a suitable period. During a non-perfusion mode the cuffs and balloon are deflated. The catheter has at least two regions, namely, guide wire and fluid delivery regions. Optionally, a separate balloon inflation region may be provided.

7 Claims, 12 Drawing Sheets

SYSTEM, METHODS AND APPARATUS FOR CEREBRAL PROTECTION

CROSS REFERENCE TO RELATED APPLICATIONS

This application claims the benefit of provisional application Ser. No. 60/555,221, filed on Mar. 22, 2004, the teachings of which are incorporated herein by reference.

The present invention relates generally to medical devices and methods including catheters, systems and methods for maintaining effective retrograde perfusion to the cerebral circulation during global or focal cerebral ischemia.

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. By contrast, focal cerebral ischemia refers to reduction of blood flow to a specific area(s) of the brain. Shock is the state in which failure of the circulatory system to maintain adequate cellular perfusion results in reduction of oxygen and nutrients to tissues. Typically within minutes of circulatory failure, tissues become ischemic, particularly in the brain.

In both global and focal ischemia, patients develop neurologic deficits due to the reduction in cerebral blood flow. Treatments should include measures to increase blood flow to the cerebral vasculature to maintain viability of neural tissue, thereby increasing the length of time available for interventional treatment and minimizing neurologic deficit while waiting for resolution of the ischemia. Augmenting blood flow to the cerebral vasculature is not only useful in treating cerebral ischemia, but may also be useful during interventional procedures, such as carotid angioplasty, stenting or endarterectomy, which might otherwise result in focal cerebral ischemia.

Anoxic brain injury results in permanent neural tissue death after only as little as five minutes in normothermic conditions. Such conditions can occur during a multitude of clinical settings such as either embolic or ischemic cerebrovascular accidents; intraoperative, septic or hemorrhagic hypotension and shock; as well as during cardiac, aortic, vascular and intracranial surgery. These conditions represent one of the leading causes of deaths in the population and currently define brain death.

During the last three decades, physicians and scientists from different specialties have been interested and involved in the research of cerebral protection. Their focus has been as diverse as their suggested solutions.

Vascular surgeons have focused on the delivery side of the equation by employing blood thinning agents such as aspirin and heparin. They have also utilized numerous intracarotid shunt devices to enhance cerebral protection during carotid endarterectomy surgery by maintaining antegrade perfusion.

Neurologists and neurosurgeons have focused mostly on the demand side of the equation by utilizing thrombolytic therapy and pharmacologic agents such as Phenobarbital that decrease the metabolic demands of the brain. They have occasionally also used some intraoperative hypothermia.

The most significant contribution to cerebral protection has however been made by cardiovascular surgeons and researchers since they have focused on both the delivery and the demand sides of the overall equation. Their long standing work with cold cardioplegia solutions, severe hypothermia and circulatory arrest during cardiac and aortic surgery have led the way to appreciating the importance of hypothermia and the use of cold retrograde blood perfusion through the venous system in providing significant cerebral protection. Furthermore, it was noted that during circulatory arrest performed for the resection of ascending aortic aneurysms, to protect the brain with both systemic hypothermia and also retrograde cold blood perfusion through the superior vena cava (SVC), part of that cold venous blood was being diverted to both upper extremities through the subclavian veins.

It was therefore suggested to apply bilateral blood pressure cuffs to both arms during the circulatory arrest and inflating them to eighty to a hundred millimeters of mercury. This would result in most of the cold blood being diverted to the brain resulting in better perfusion and better cooling of the brain during circulatory arrest and translating into better cerebral protection.

This concept was tried clinically on a series of patients. Their circulatory arrest temperatures ranged from 25 to 27 degrees Celsius instead of the normal 16 to 18 degrees Celsius, a full ten degrees warmer. Higher temperatures were tolerated mainly due to the better perfusion of cold blood to the brain, thus alleviating the need for even colder blood. This, of course, resulted in less time to cool the body temperature down and less time to resuscitate the patient and significantly less complication rates overall. Their circulatory arrest period ranged from twenty-nine to sixty-seven minutes. There was universal cerebral protection with no neurologic deficits. The retrograde cold blood perfused also had a temperature of 25 to 27 degrees Celsius. This concept of cerebral protection has been extended to the fields of medical and surgical treatment of cerebrovascular accidents whether due to embolic, ischemic or hemorrhagic (cerebral aneurysms and arteriovenous malformations) events.

According to the present invention, methods, systems and devices are provided for perfusing a brain territory, retrogradely, which is ischemic, through its venous drainage system.

According to one embodiment, a method is provided to maintain or increase cerebral perfusion during global or focal cerebral ischemia, for example. The method perfuses an oxygenated medium, e.g., blood, in the cerebral vascalature of a patient. For example, increased cerebral perfusion or blood flow retrogradely is provided during global or focal cerebral ischemia. The method includes: (1) positioning left and right pressure cuffs on the respective left and right upper extremities of a patient; (2) providing a catheter having a multi-configuration, the catheter having a proximal region, a distal region, and an expandable member, e.g., a balloon, which is circumferentially disposed and sealably attached about the catheter and mounted substantially adjacent or near the distal end of the catheter; (3) inserting the catheter into a subclavian vein of the patient; alternatively, the catheter may be introduced through the femoral vein, also in a conventional manner; (4) advancing the catheter through the (right or left) subclavian (or right or left femoral vein) such that the expandable member is positioned to occlude the superior vena cava substantially proximal to the take-off of the left inominate vein of the patient.

During a perfusion mode of a perfusion/non-perfusion cycle, the following operations are performed: (1) inflating the left and right pressure cuffs, e.g., to substantially 80 to 100 millimeters of mercury; (2) expanding the member to cover a substantial portion of the cross-sectional area of the superior vena cava causing an increase in cerebral blood flow, retrogradely; and (3) pumping the oxygenated medium from a femoral artery into the catheter for a period, such as a number of (EKG) beats, for example approximately in the range from 2 to 32 or 2 to 100, or any other suitable period. The period may be variable as needed. The catheter may include a second expandable member, e.g., a balloon, circumferentially disposed and sealably attached around a second portion of the catheter substantially adjacent or near the proximal end of the catheter so that the second balloon is positioned near the insertion site. The second balloon is configured to inflate during the perfusion mode to prevent back bleeding from the insertion site. Both or one of the balloons may be self-inflating normal type or a parachute type balloon. During a non-perfusion mode of the perfusion/non-perfusion cycle, the following operations are performed: (1) deflating the left and right pressure cuffs; and (2) collapsing the expanded member. Further operations include coating the catheter with anti-thrombogenic material such as heparin, and using the catheter to measure the central venous pressure in the superior vena cava during both or one of the perfusion and non-perfusion modes. Successive perfusion/non-perfusion cycles may be performed until, for example, a clot in a patient's arterial system is dissolved by thrombolysis, or a ruptured cerebral aneurysm is clipped or endovascularly coiled. The central venous pressure in the superior vena cava may be measured during one or both the perfusion mode and non-perfusion mode.

According to another aspect, a system for providing cerebral protection comprises, according to one embodiment, one or more catheters for selectively perfusing, in various embodiments, the brain through its venous drainage system by SVC occlusion. The catheters can be inserted through an insertion site of either the (right or left) subclavian vein or the (right or left) femoral vein. A combination of both subclavian and femoral veins can be also used. Such systems include a pump, one or more occluding balloons, an EKG monitor and a processor.

A system may optionally include a cooling device to cool the arterial blood, e.g., from a femoral artery, while it is being pumped by a pump into the subclavian vein or the femoral vein. That is, in addition to maintaining and/or improving cerebral perfusion, the method according to one embodiment may combine or otherwise rely on cooling of the cerebral vasculature in treatment of both global and focal cerebral ischemia to inhibit or minimize tissue damage resulting from lack or limitation of cerebral blood circulation. In use, the oxygenated medium that is circulated will be cooled in order to cool the brain tissue and reduce the risk of ischemic damage.

These and other aspects will become apparent to those skilled in the art upon reading the following detailed description in conjunction with the following drawings.

Referring now to the drawings in which like reference numbers represent corresponding parts throughout, where:

Figure 4A:
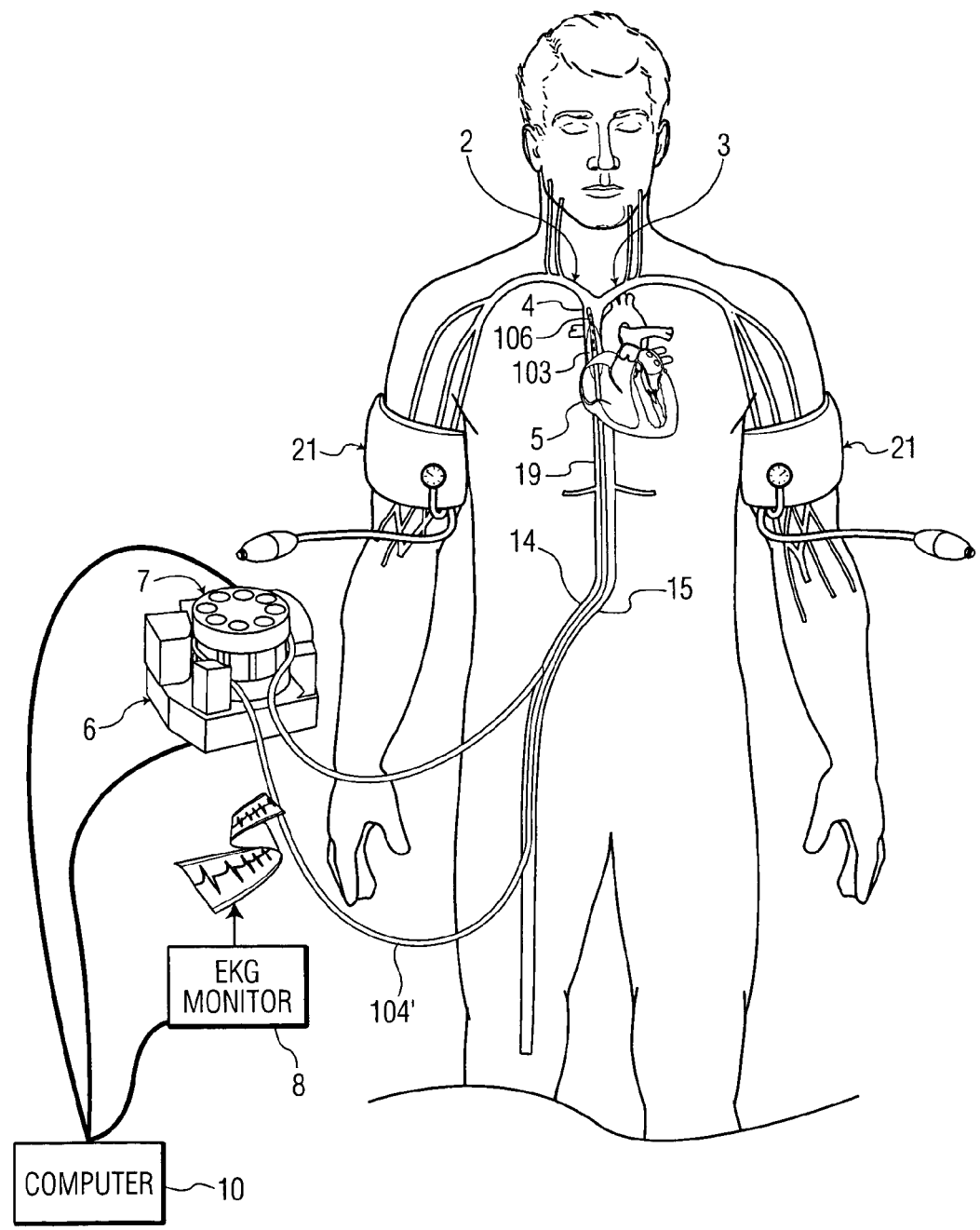
FIG. 4a is an illustration of the system according to another embodiment.
Figure 4B:
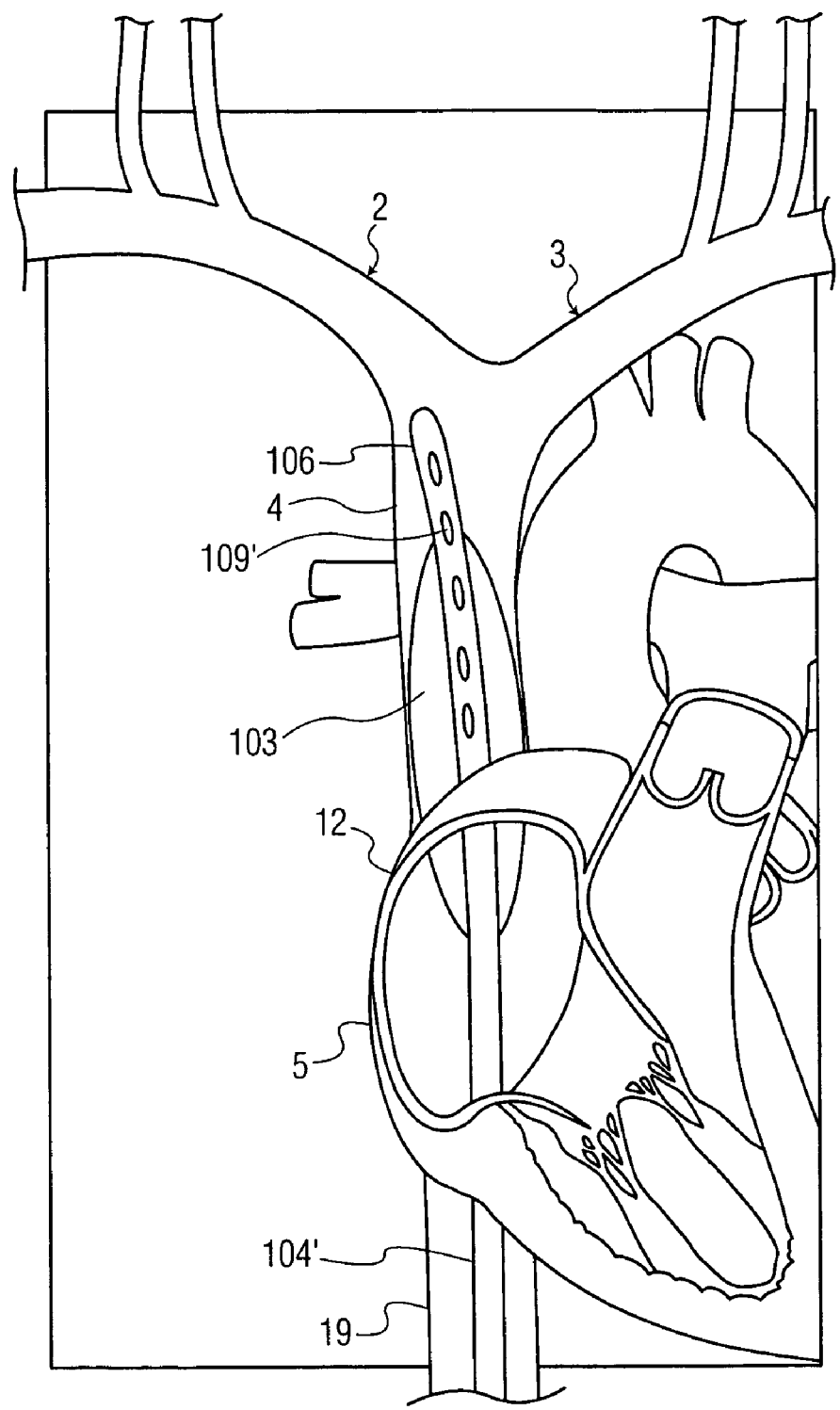
Figure 5A:
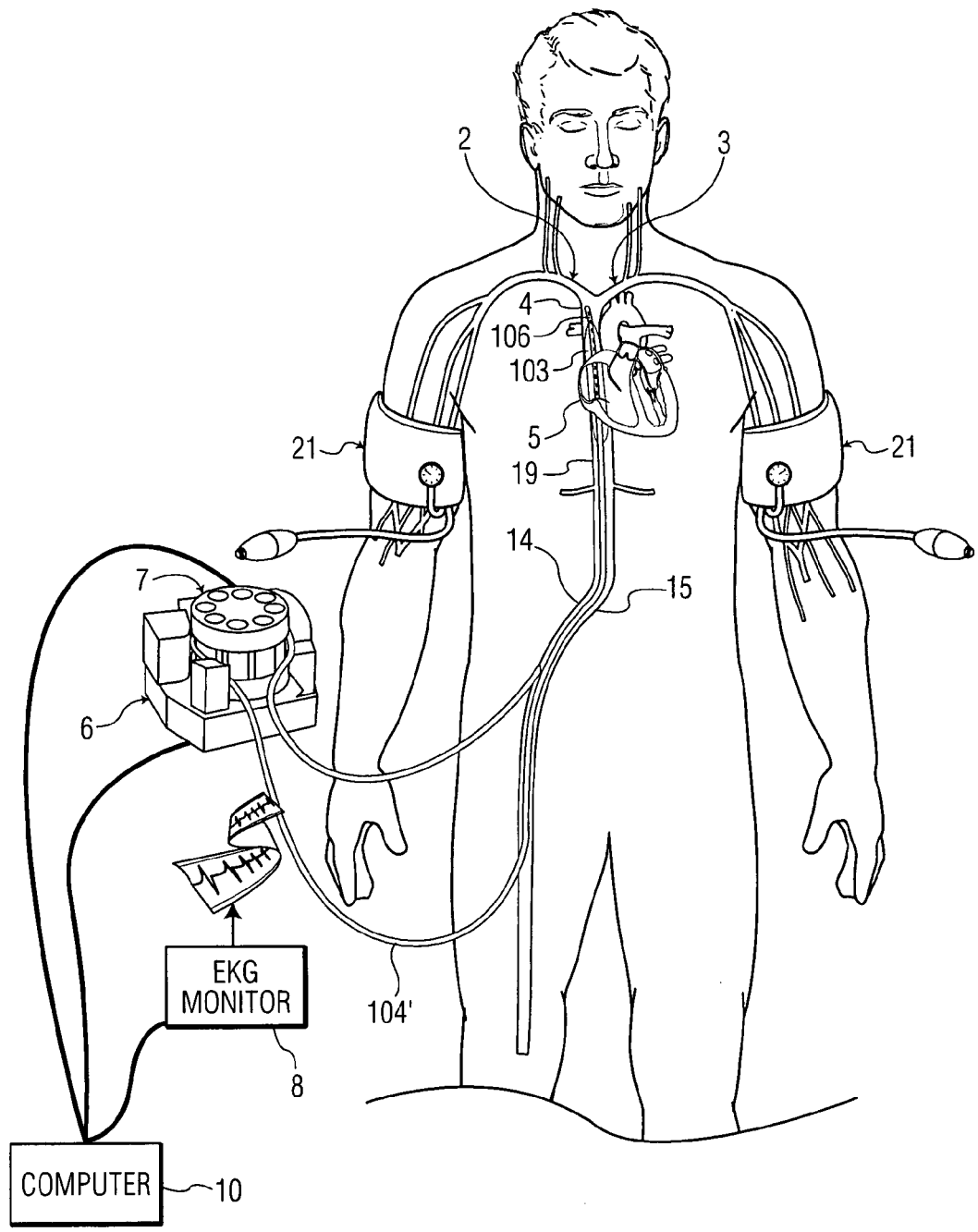
Figure 5B:
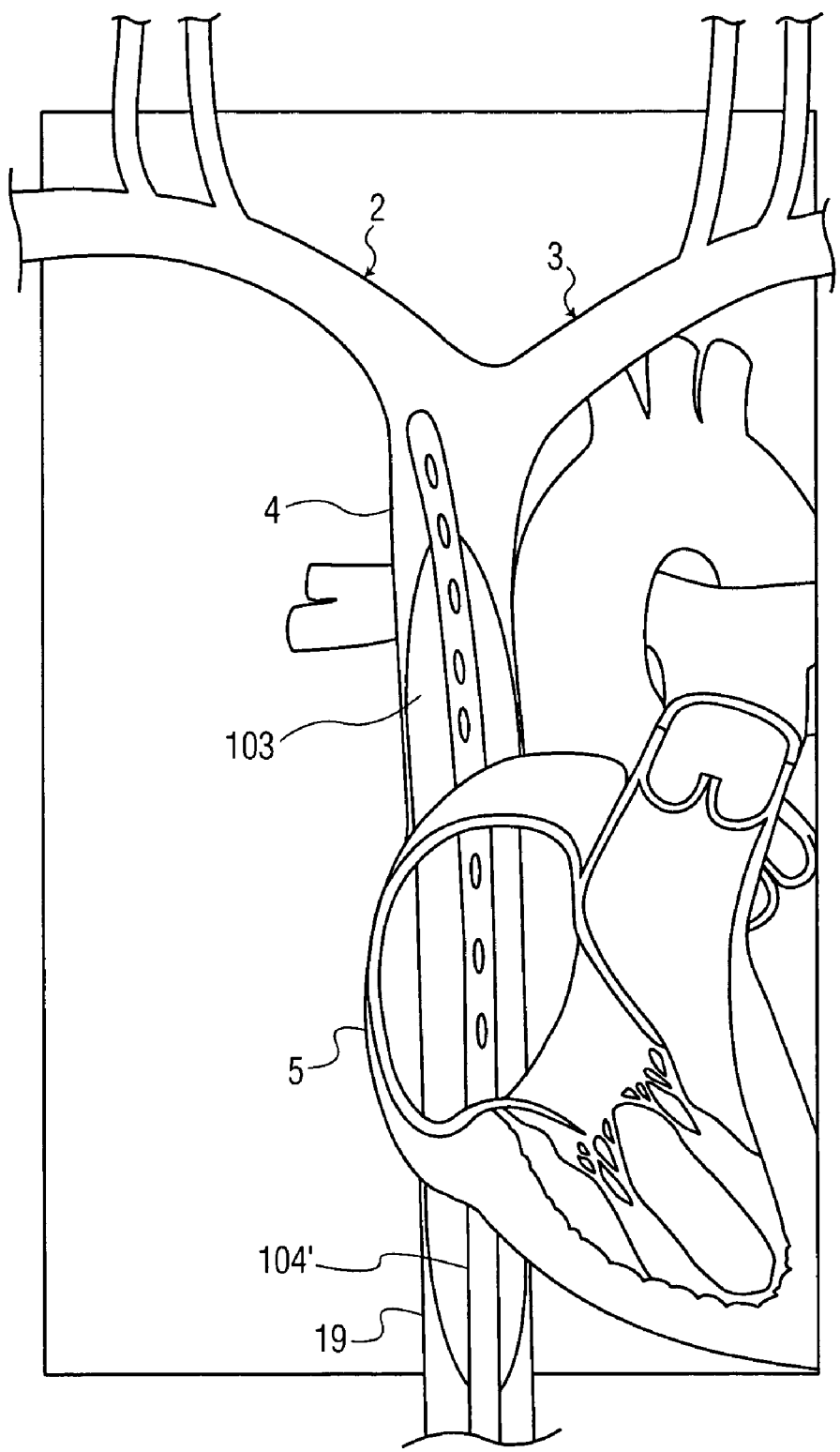
Figure 6:
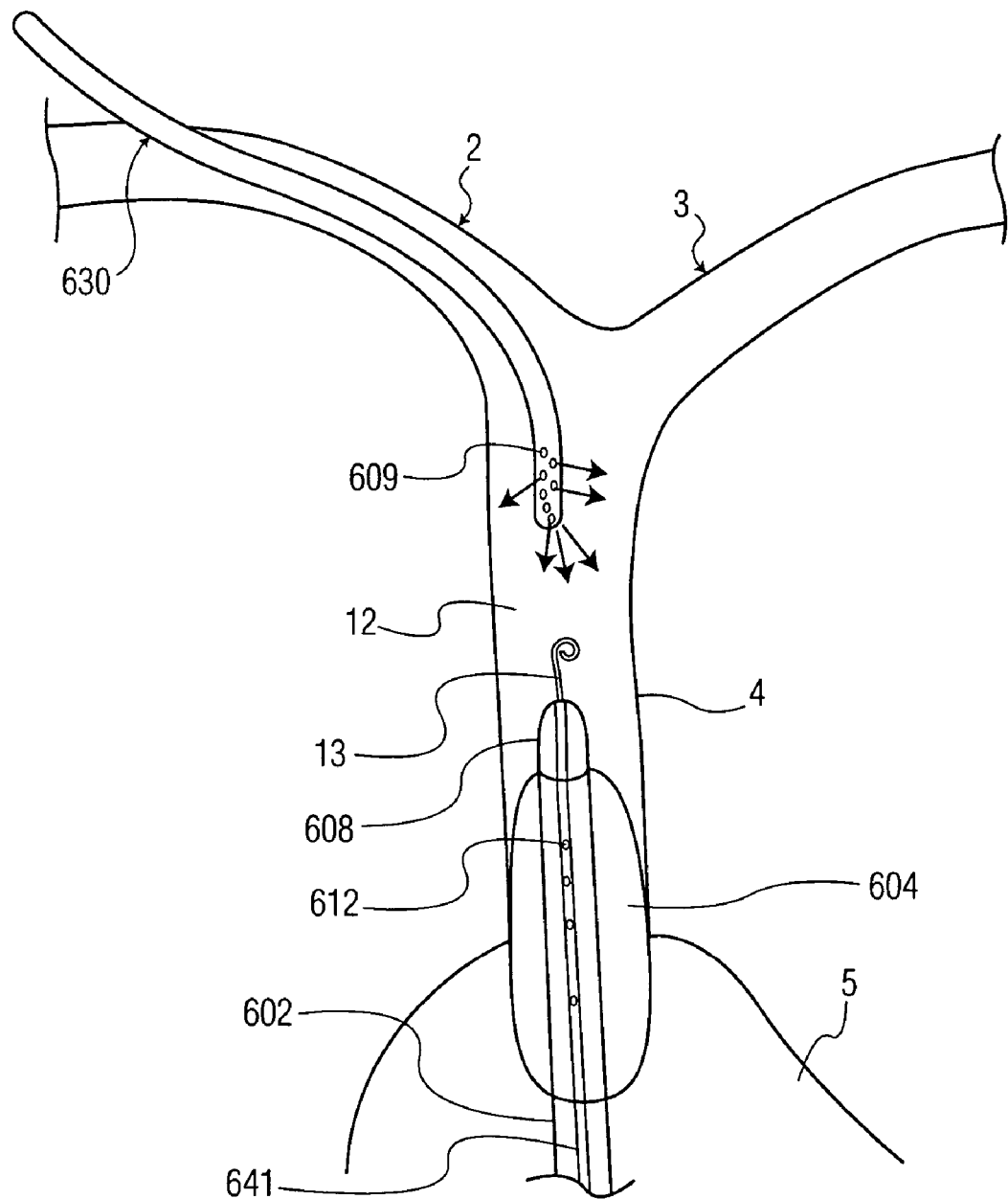

FIG. 4b is an illustration of a zoom view of the chest region of the human being illustrated in FIG. 4a, FIG. 5a illustrates an embodiment using a balloon for providing simultaneous occlusion of both the superior vena cava and inferior vena cava; and FIG. 5b is an illustration of a zoom view of the chest region of the human being illustrated in FIG. 5a, FIG. 6 is an illustration of another system according to another embodiment.

In the following description of the specific embodiments, reference is made to the accompanying drawings which form a part hereof and which show by way of illustration various embodiments in which the invention may be practiced. In the accompanying drawings, like reference numbers represent corresponding parts throughout the several views. It is to be understood that other embodiments may be utilized as structural changes may be made without departing from the scope of the invention.

The devices and methods disclosed herein are most useful in treating patients suffering from global cerebral ischemia and focal cerebral ischemia. However, it will be understood that the devices and methods can be used in other medical conditions.

The remainder of the detailed description is organized in the following manner.

First, an overview of the principles according to the present invention is provided in accordance with the various embodiments.

Second, a detailed description is provided of the elongate catheter for both a two-region and a three-region embodiments.

Third, a detailed description is provided according to a first embodiment describing a single catheter/single balloon arrangement.

Fourth, a detailed description is provided according to a second embodiment describing a single catheter/two balloon arrangement.

Fifth, a detailed description of an alternate embodiment of the short self inflation balloon is described.

Sixth, a detailed description is provided according to a third embodiment, which utilizes a femoral catheter for insertion through a femoral vein.

Seventh, a detailed description is provided according to a fourth embodiment. which utilizes an extended femoral catheter for insertion through a femoral vein to simultaneously occlude both the superior and inferior vena cava.

Eighth, a detailed description is provided according to a fifth embodiment which utilizes both a femoral catheter and sub-clavian catheter.

Ninth, a detailed description is provided according to a sixth embodiment in which the two catheter arrangement of the fifth embodiment further includes a short self inflation balloon on the sub-clavian catheter.

I. OVERVIEW

In accordance with the various embodiments, the brain and associated neurologic tissues remain intact, throughout efforts to provide an oxygenated medium, retrogradedly to the brain territory, which is ischemic, through its venous drainage thereby prolonging the survival time of the exposed neural tissue until either the culprit clot in the arterial system is dissolved by thrombolysis or the culprit ruptured cerebral aneurysm has been clipped, endovascularly coiled, or otherwise repaired. As referred herein, the cerebral vasculature includes all arteries and veins leading into or from the patient's head, particularly including the common carotid arteries, the external and internal carotid arteries, and all smaller arteries which branch from the main arteries leading into the head.

Patients suffering from ischemia resulting from acute or chronic occlusion in the cerebral vasculature may be treated according to the embodiments described below. Each of the embodiments described herein are generally directed to increasing retrograde perfusion to the brain, minimizing venous congestion in the superior vena cava, and maximizing cerebral protection. As will be clear to those skilled in the art, increased retrograde perfusion is achieved when a balloon is inflated in the SVC forcing increased retrograde blood flow to the brain. Various embodiments share a common feature namely a sequence of perfusion/non-perfusion cycles that repeat.

It should be noted that for each of the embodiments, the catheter(s) may be introduced using percutaneous insertion, (Seldinger technique over a guide wire), or other insertion techniques. It is also noted that for each of the embodiments, the catheters are capable of measuring the central venous pressure in the superior vena cava during both the perfusion and non-perfusion modes.

Figure 1A:
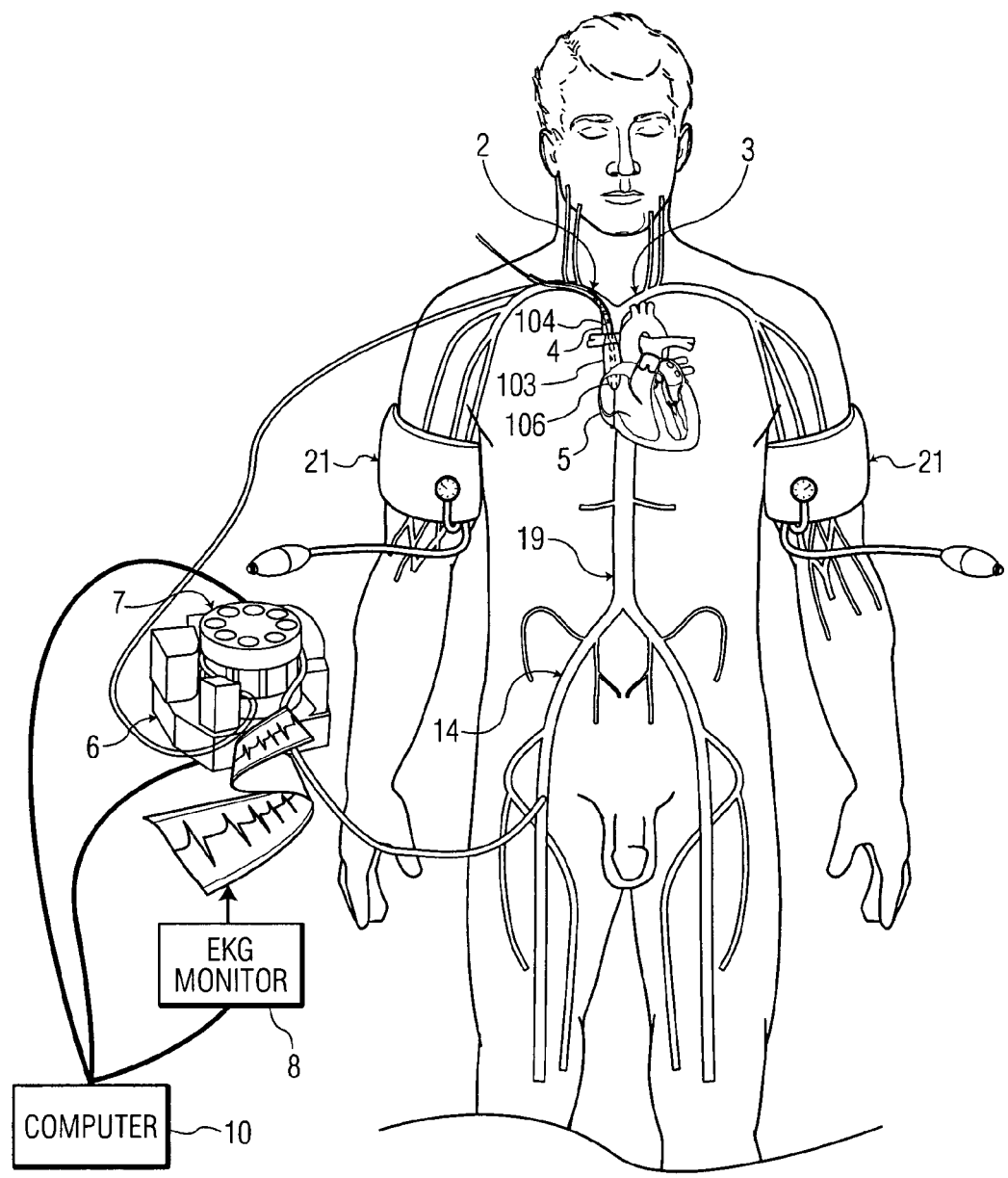
FIG. 1A is an illustration of the system according to one embodiment.
Figure 1B:
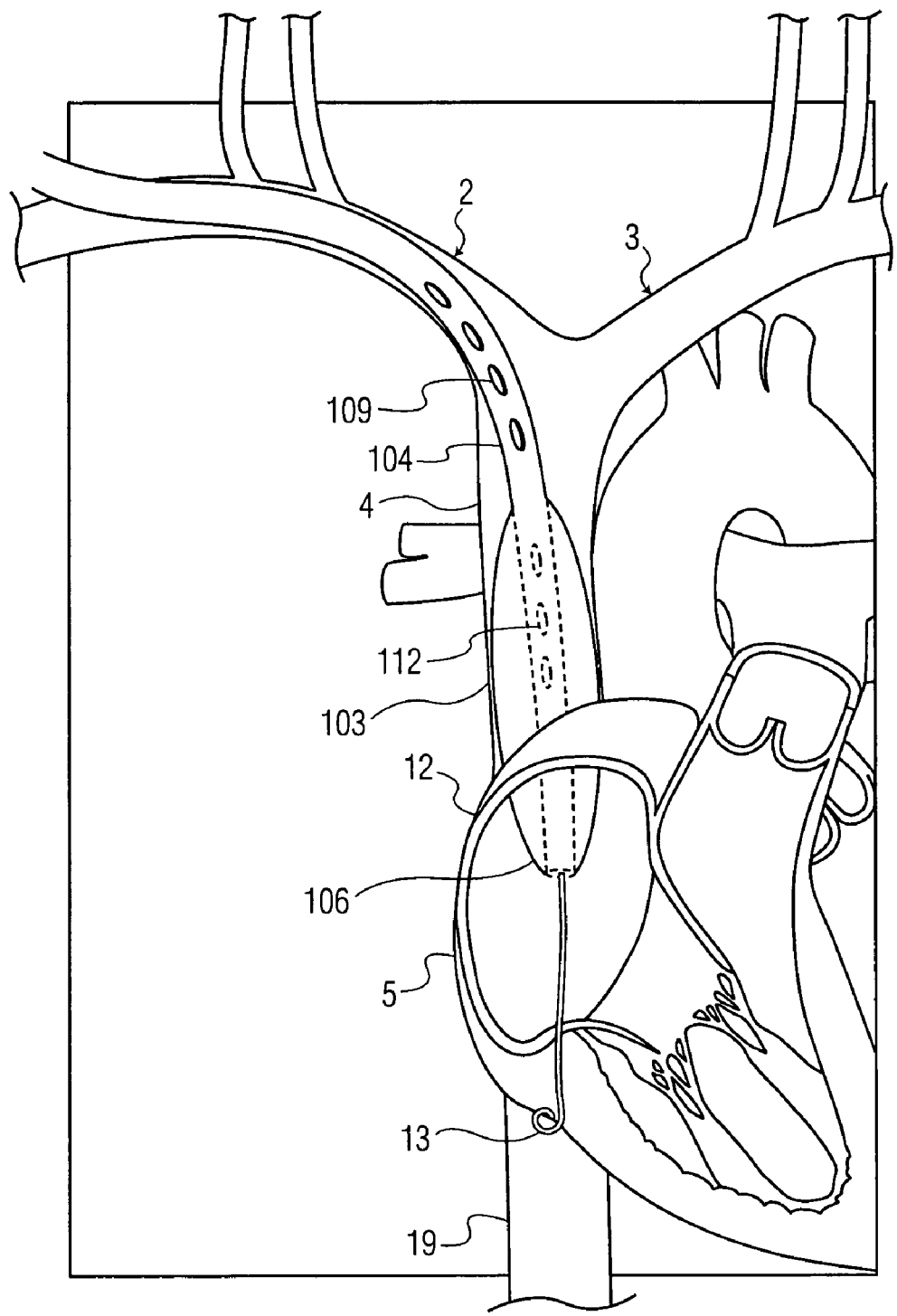
FIG. 1B is a zoom view of the thoracic region of FIG. 1A.

Various embodiments will now be described in detail with reference to the accompanying drawings. With reference to the drawings, and in particular FIGS. 1A and 1B, there is illustrated a method and system, according to one embodiment, for perfusing the cerebral circulation retrogradely by inserting the catheter through either the right or left subclavian vein.

In the present embodiment, as shown in FIG. 1A and more particularly in FIG. 1B which shows a zoom view of the thoracic region of FIG. 1A, an elongate intravascular catheter 104 is shown having a proximal end and a distal end, shown here positioned within the patient's superior vena cava 4. The distal end includes an expandable member 103. Illustratively, the elongate catheter 104 has a tubular body.

Prior to discussing the various embodiments disclosed herein directed to systems and methods, it is instructive to first discuss the various embodiments of the elongate catheter 104.

II. ELONGATE CATHETER

Figure 1C:
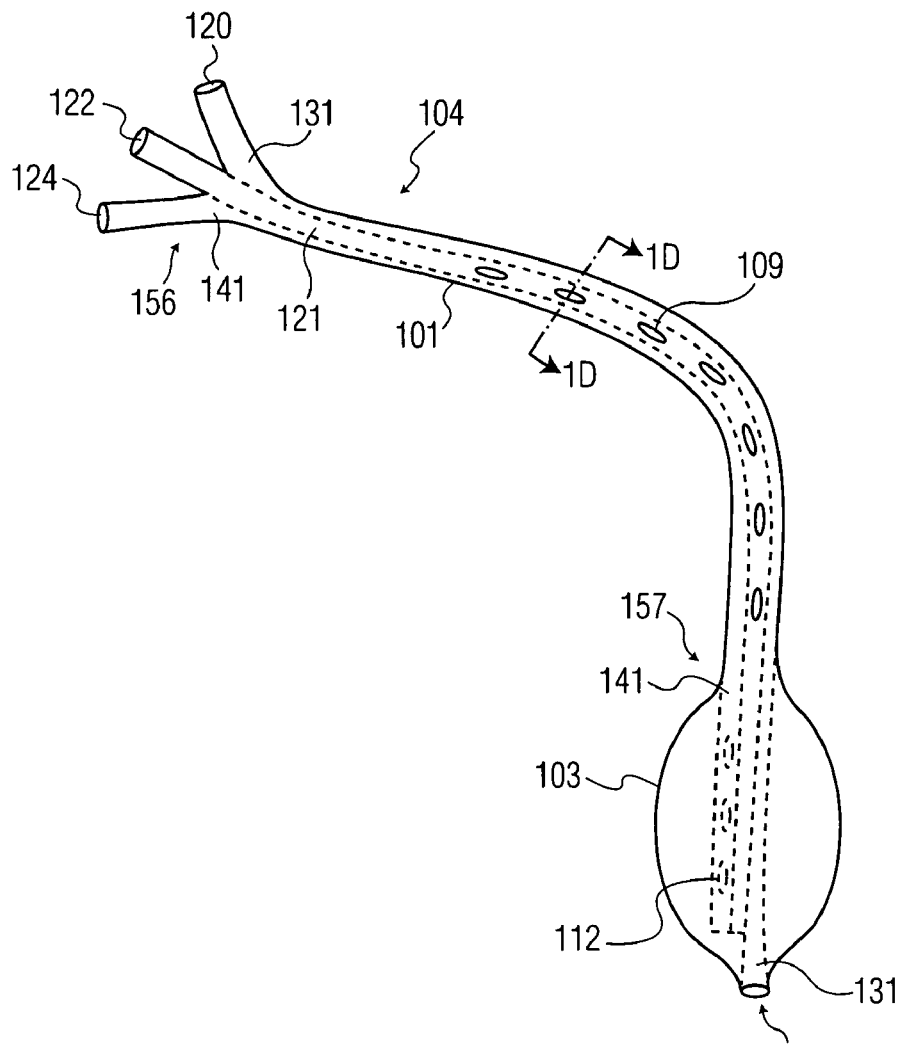
FIG. 1C is an illustration of an elongate catheter having a catheter body comprised of three regions according to another embodiment.
Figure 1D:
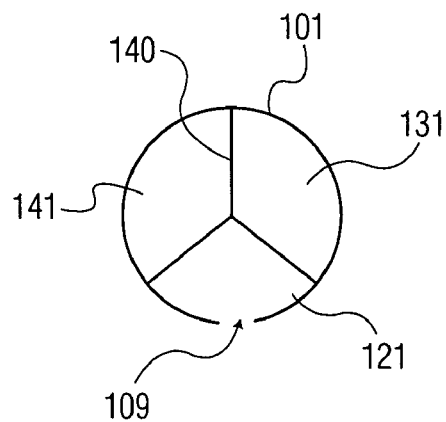
FIG. 1D is a magnified lateral cross section of the catheter of FIG. 1C taken along line 2-2.
Figure 1E:
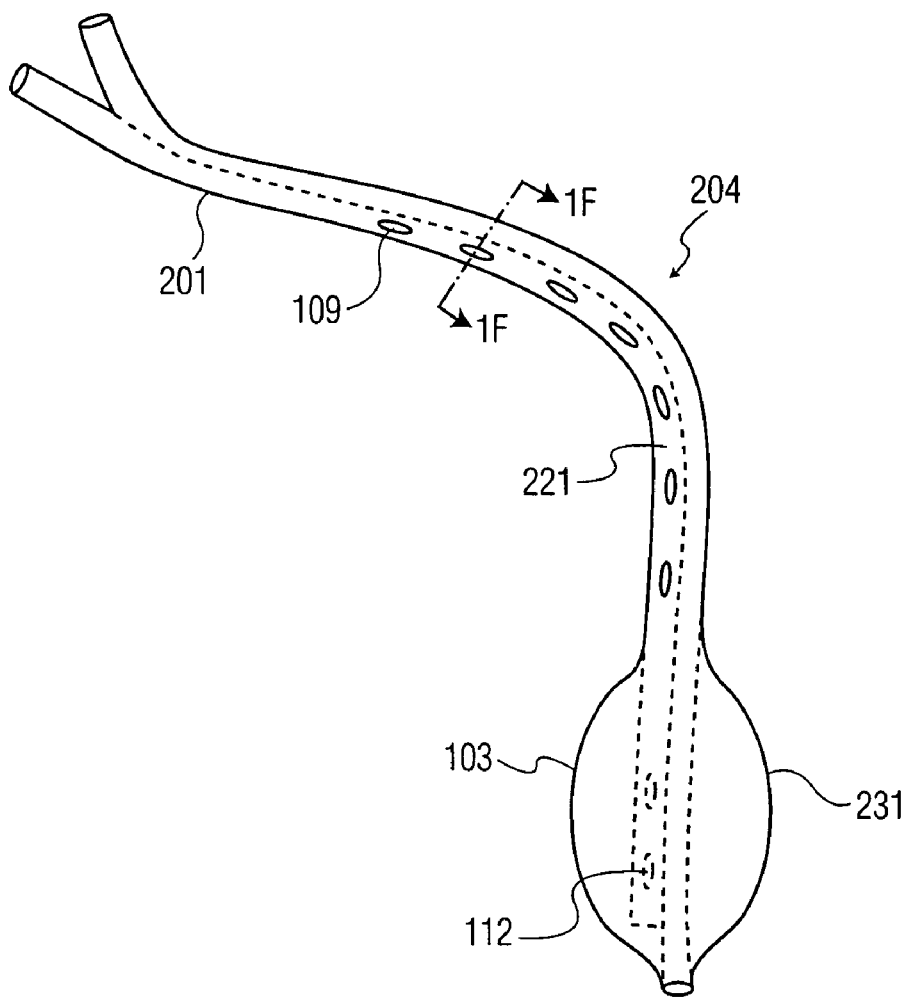
FIG. 1E is an illustration of an elongate catheter having a catheter body comprised of two regions.
Figure 1F:
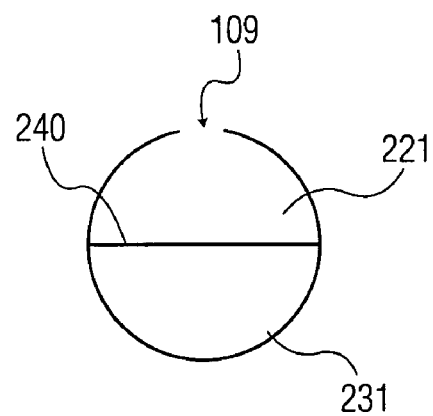
FIG. 1F is a magnified lateral cross section of the catheter of FIG. 1E taken along line 3-3.

FIGS. 1C and 1D illustrate a first embodiment of an elongate catheter 104 and FIGS. 1E and 1F illustrate a second embodiment of another elongate catheter 204. It should be understood that in each of the two embodiments to be described, the elongate catheter 104, 204 is comprised of a catheter body 101, 201 having a multi-region internal configuration (see FIGS. 1D and 1F). The two embodiments differ, however, in the number of constituent regions. That is, the first embodiment is directed to a catheter 104 divided internally into three regions (see FIG. 1D) and the second embodiment is directed to a catheter 204 divided internally into two regions (see FIG. 1F), as will be described.

II-A Three-Region Catheter

Referring first to FIGS. 1C and 1D, a first exemplary embodiment of the elongate catheter 104 is shown. In this embodiment, the elongate catheter 104 is shown having a catheter body 101 comprised of a single tubular member including a generally "Y" shaped internal dividing wall 140 (see FIG. 1D) dividing the interior of the catheter body 101 into first 121, second 131 and third 141 internal regions, to be described below with reference to FIG. 1D. The size of each region need not be similar in which case the cross section of the internal dividing wall 140 would deviate from the "Y" shape shown in FIG. 1D.

The catheter body 101 should be of sufficient length to reach from an insertion point at either the right or left subclavian vein of a patient to a distant location residing at very close proximity to the atrial-superior vena cava junction. With the aforementioned length requirements in mind, the overall length of the catheter 104 is preferably approximately 10 cm to 30 cm, or any other desirable length. The total outside diameter of the catheter tubular body 101 should be of minimal size, but of sufficient internal diameter to be able to provide adequate fluid flow. With the aforementioned diameter requirements in mind, the outside diameter of the catheter tubular body 101 is preferably approximately 2 French to 24 French, or any other desirable diameter.

Illustratively, the elongate catheter 104 is formed from a flexible thermoplastic material, a thermoplastic elastomer or a thermoset elastomer. More specifically, suitable materials for the elongate catheter 104 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the elongate catheter 104 may be made of thin walled metallic tubing or hypotube, such as stainless steel, platinum, titanium, nitinol or Cobalt alloys such as Elgiloy and Carpenter MP 35.

Furthermore, the catheter 104 may be coated with lubricious coatings that aid in the insertion and removal of the catheter as well as aid in hemocompatibility and anticoagulation. The coatings, which may be external or internal to the catheter 104, are nonreactive, hydrophilic or hydrophobic. Medicated coatings may also be incorporated which are antithrombogenic, antimicrobial, anticancer, antigrowth factor, growth factor or anti-inflammatory. Examples of such coating are SLIP-COAT and MEDI-COAT made by STS Polymers Henrietta, N.Y. In addition, the shaft may be coated with echogenic material such as ECHO-COAT also made by STS Polymers Henrietta, N.Y. to aid in tracking and placement of the device with the use of ultrasound.

FIG. 1D shows a lateral cross section of the catheter tubular body 101 of FIG. 1C taken along line 1D-1D. FIG. 1D illustrates that that the catheter body 101 is divided into three regions by the internal dividing wall 140, namely, a fluid delivery region 121, a guide wire region 131 and a balloon inflation region 141. The guide wire region 131 is sized and configured to assist in the initial placement of a guide wire (shown as reference numeral 13 in FIG. 1B). The balloon inflation region 141 is sized and configured to inflate the balloon 103. The fluid delivery region 121 is sized and configured to deliver oxygenated medium from a patient's femoral artery into the patient's cerebral vascalature. Each region 121, 131, 141 is described in greater detail as follows.

Guide Wire Region 131

The guide wire region 131 has dimensions and characteristics suitable for introducing a guide wire to the desired intravascular target site. The guide wire region 131 is a portion of the catheter tubular body 101 separated from the inflation region 141 and fluid delivery region 121, by the dividing wall 140. The guide wire region 131 has an associated guide wire port 120 (as shown in FIG. 1C) which mates with the guide wire region 131 at the proximal end 156 of the catheter tubular body 101. The guide wire region 131 and its associated guide wire port 120 are dimensioned to slidably receive an elongated flexible guide wire therethrough (shown as numeral 13 in FIG. 1B). The balloon 103 is circumferentially disposed and sealably attached to the catheter tubular body 101, leaving the distal end 155 of the guide wire region 131 exposed so that the flexible guide wire passes therethrough as shown by numeral 13 in FIG. 1B, for example. That is, the distal end 155 of the guide wire regions 131 is open. By contrast, the distal ends of the balloon inflation region 141 and the fluid delivery region 121 are closed. The guide wire region 131 constitutes generally on the order of 10% of the total internal diameter or any other diameter of the internal catheter tubular body 101 (not shown to scale in FIG. 1D).

Balloon Inflation Region 141

The balloon inflation region 141 is a region of the catheter tubular body 101 separated from the guide wire region 131 and the fluid delivery region 121 by dividing wall 140. The balloon inflation region 141 has an associated inflation port 124 (as shown in FIG. 1C) which mates with the balloon inflation region 141 at the proximal end 156 of the catheter tubular body 101. The balloon inflation region is closed at a distal end 157 of the catheter tubular body 101. The balloon inflation region constitutes generally on the order of 20% of the total internal diameter or any other desired diameter of the internal catheter tubular body 101 (not shown to scale in FIG. 1D). The balloon inflation region 141 has the inflatable occlusion balloon 103 circumferentially disposed and sealably attached about the distal end 157 of the catheter tubular body 101. The inflatable occlusion balloon 103 may be any conventional type of balloon commonly used for blood region occlusion, e.g., elastomeric balloons having a generally spherical geometry. The inflatable occlusion balloon 103 is sized to access and occlude the superior vena cava 4 and is collapsible to facilitate insertion into and removal from a vessel, and expandable during use to restrict blood flow. When expanded, the inflatable occlusion balloon 103 has a maximum periphery that conforms to the inner wall of the vessel, thereby providing a sealed contact between it and the vessel wall.

At the distal end 157, the balloon inflation region 141 has perfusion ports 112 for inflation and deflation of the balloon 103 through the pumping and suction action of an inflation pump which is typically different from the roller pump 7 shown in FIG. 1A. The inflation pump is synchronized with the perfusion and non-perfusion modes as will be described, and may pump gas or liquid, such as helium or saline for example, to expand the balloon 103 in the perfusion mode to retrogradely perfuse the patient's cerebral vasculature. Reverse operation of the inflation pump deflates the balloon 103 in the non-perfusion mode to allow drainage of blood to the right atrium. The inflatable occlusion balloon 103 will be expandable to a size in the range from 5 mm to 50 mm, or any other desired diameter, typically at a relatively low inflation pressure.

It will be understood that the inflatable occlusion balloon 103 can be of any shape that is suitable for use in the superior vena cava 4. For example, the inflatable occlusion balloon 103 can be elliptical or sausage-shaped, which is particularly desirable because this shape is more stable within rapidly flowing blood. A spherical balloon (although useful) will tend to rock within the superior vena cava 4, and rotate and bend the catheter to which it is affixed. The use of an elongate balloon, however, reduces the rocking and rotating within the vessel because this shape effectively eliminates one of the degrees of freedom present with a spherical balloon.

It may be appreciated that the inflatable occlusion balloon 103 may be inflated with a number of materials, including suitable liquids such as saline, blood, gas such as helium, expanding foam, and/or adhesive, to name a few.

Fluid Delivery Region 121

The fluid delivery region 121 is a region of the catheter tubular body 101 separated from the guide wire region 131 and the inflation region 141 by the dividing wall 140. The fluid delivery region 121 has an associated fluid delivery port 122 (as shown in FIG. 1C) which mates with the fluid delivery region 121 at the proximal end 156 of the catheter tubular body 101. The fluid delivery region 121 couples blood from the patient's artery, e.g., the femoral artery 14 (see FIG. 1A) into the patient's cerebral vascalature under control of an external pump 7 which is substantially synchronized with the inflatable occlusion balloon 103 in an inflated state. The fluid delivery region 121 has perfusion ports 109 which are located before, e.g., proximal to, the balloon 103 and allow blood from the patient's femoral artery to perfuse into the patient's cerebral vasculature retrogradely. The diameter of the fluid delivery region 121 constitutes generally on the order of 70% of the total internal diameter or any other desired diameter of the internal catheter tubular body 101 (not shown to scale in FIG. 1D).

The inner surface of the fluid delivery region 121 has a coating as described herein which covers or is impregnated with at least one pharmaceutical compound or drug adapted to be released over time that affect the blood flowing through the fluid delivery region 121 in a desired way. For example, a heparin or other coating may be used that will reduce clot formation in the patient's cerebral vessels through which the catheter extends. Examples of commercially available heparin coatings that may be used include heparin-benzalkonium chloride complex, heparin-TDMAC complex and other medical coatings available from STS Biopolymers, Inc. 336 Summit Point Dr., Henrietta, N.Y.

By exposing such coated a surface to the blood stream of a living being, the pharmaceutical compound is released from the coating in a controlled manner while retaining other non-volatile decomposition products within the coating. The coating may be about 0.1-1.0 mm thick, or any other desired thickness, and may contain about 1-100 micromoles of a pharmaceutical releasing compound per $mm^2$, or any other desired concentrations or rates. For example, higher concentrations can be used when different diffusion rate of the pharmaceutical compound and/or longer release of the pharmaceutical compound are desired.

II-B Two-Region Catheter

Referring now to FIGS. 1E and 1F, a second exemplary embodiment of elongate catheter 204 is shown. In this embodiment, elongate catheter 204 is shown having a catheter body 201 comprised of a single tubular member including a dividing wall 240 internally dividing the interior of the catheter body 201 into first and second internal regions, i.e., a fluid delivery region 221 and a guide wire region 231, (as shown in FIG. 1F which is the cross-section view of the catheter body 201 of FIG. 1E taken along line 1F-1F). In this embodiment, the elongate catheter 204 is shown having a catheter body 201. The diameter of the fluid delivery region 221 constitutes generally on the order of 70% of the total internal diameter or any other desired diameter of the internal catheter tubular body 101 (not shown to scale).

The guide wire region 231 is substantially identical to the guide wire region 131 described above in connection with the three-region catheter 104 embodiment described above, and illustrated in FIGS. 1C-1D.

The fluid delivery region 221 is similar to the fluid delivery region 121 of the three-region catheter 104 described above with the following distinction. Specifically, the two-region catheter configuration 204 is nearly identical to the three-region catheter configuration 104 described above in connection with FIGS. 1C-1D, in most respects, except that in the two-region catheter configuration 204, the fluid-delivery region 221 serves more than one function. The first function, previously described above, concerns coupling blood from the patient's femoral artery into the patient's cerebral vasculature under control of an external roller pump 7 (as shown in FIG. 1A). The second additional distinguishing function performed by the fluid delivery region 221 is to inflate the inflatable occlusion balloon 103. The astute reader will recall that this function was performed by the inflation region 141 of the three-region configuration of FIGS. 1C and 1D. In the present embodiment, the fluid-delivery region 221 performs the additional function of inflating the inflatable occlusion balloon 103 from the pressure provided from the blood flow directed from the patient's femoral artery 14 (as shown in FIG. 1A).

As shown in FIG. 1E, the fluid delivery region 221 has a first set of perfusion ports 109 which are located before, e.g., proximal to the balloon 103 and allow blood from the patient's femoral artery to perfuse into the patient's cerebral vasculature retrogradely. Also shown associated with the fluid delivery region 121 is a second set of perfusion ports 112, at the distal end of the fluid-delivery region 221 and enclosed or surrounded by the balloon 103 to allow blood from the patient's femoral artery to perfuse the inflatable occlusion balloon 103. It is noted that the second set of perfusion ports 112 may have varying sizes or diameters. This is to allow the balloon 103 to fill up with blood quickly and occlude in time to provide sufficient back pressure to allow blood from the patient's femoral artery to perfuse into the patient's cerebral vasculature retrogradely.

Having described the various configurations 104, 204 of elongate catheters, an embodiment is now described with reference to FIGS. 1A and 1B of the drawings.

III. FIRST EMBODIMENT

The present embodiment describes a method and system for selectively perfusing the brain with retrograde cold blood during acute cessation of perfusion to a specific area of the brain due to closure or lack of flow in the arterial blood supply to that segment. It is noted that in the embodiments described throughout the specification, the various methods may utilize the left subclavian vein or the right subclavian vein with equal efficacy of operation.

FIG. 1B shows a zoom view of the thoracic region of FIG. 1A showing in detail the region of insertion of the elongate catheter 104.

Referring to FIG. 1B, elongate catheter 104 is shown, for proper placement, advanced into the right atrium 5. Upon correct positioning, for example using the guide wire 13, the tip 106 of the elongate catheter 104 is placed at very close proximity to the right atrial-superior vena cava junction 12. The inflatable occlusion balloon 103 is positioned in the superior vena cava 4 just proximal to the take off of the left innominate vein 3. However, the inflatable occlusion balloon 103 should not obstruct the entrance of the left inominate vein 3. Upon sufficient inflation, the inflatable occlusion balloon 103 occludes the superior vena cava 4. It will be understood that in the perfusion mode to be described, when occlusion is applied by the inflated balloon 103, there is an increase in cerebral blood flow retrogradely allowing oxygenated medium introduced through the elongate catheter 104 to travel upwardly into the cerebral venous system. Similarly, the tourniquet(s) 21 in both upper extremities (see FIG. 1A) will be inflated in the perfusion mode to prevent the outflow of blood or other oxygenated medium into the upper extemities.

III-A Perfusion/Non-Perfusion Modes

In accordance with a method according to an exemplary embodiment, a single cycle of operation is now described comprising two modes, a perfusion mode (i.e., arterial blood pumping mode) and a non-perfusion mode. It should be appreciated, however, that operation over multiple cycles is performed in the various embodiments described herein.

(A.) Perfusion Mode (Pumping Period)

During the perfusion mode, the inflatable occlusion balloon 103 is expanded (inflated), for example by femoral blood from the femoral artery 14 (FIG. 1A) pumped by the roller pump 7 using the two-region catheter 204, or when using the three-region catheter 104, by other fluids (e.g., gas such as helium or liquid such as saline) pumped by another pump, as described above. The balloon is expanded or inflated to occlude the superior vena cava 4 substantially simultaneous in time with the subclavian catheter 104 being perfused with arterial blood from the patient's femoral artery 14. The arterial blood perfuses the subclavian catheter 104 with the aid of a roller pump 7 (see FIG. 1A) which pumps arterial blood from the patient's femoral artery 14 to the subclavian vein 2. The roller pump 7 pushes blood from the femoral artery 14 to the subclavian vein 2 for a certain period such as anywhere from 2 to 100 EKG beats (e.g., QRS Complexes) in each cycle. In one embodiment, the range is substantially from 2 to 32 EKG beats. As shown in FIG. 1A, the roller pump 7 is attached in series to a cooling device 6 that allows the femoral arterial blood to cool down to temperatures substantially in the range of 25 to 27 degrees Celsius, for example. Of course, the femoral arterial blood may be cooled to other desired temperatures including but not limited to the range between 16 to 18 or 16 to 34 degrees Celsius. The cooled down blood is pumped by the roller pump 7 through the subclavian catheter 104 into the superior vena cava 4 via the right or left subclavian vein 2.

As shown in FIG. 1A, the roller pump 7 and the patient's EKG monitor 8 are connected and synchronized to a computer (processor or controller) 10 which controls the frequency of perfusion/non-perfusion cycles. The EKG monitor 8 is operable to detect the QRS complex in the patient's heart cycle, for example. The EKG monitor 8 computes an average time period between successive QRS complexes and initiates a timing cycle for pumping the blood through the subclavian catheter 104 into the superior vena cava 4 via the right subclavian vein 2, using the roller pump 7. After detection of a QRS complex and a time delay to account for the travel time of the pulse volume into the leg, the EKG monitor sends an electrical output signal to the roller pump 7 to pump blood through the subclavian catheter 104 into the superior vena cava 4 via the right subclavian vein 2. It is noted that, instead of detecting the QRS complex, the EKG monitor 8 may alternatively detect various other parts of the characteristic pattern of the heart waveform, including portions (or arterial BP) of a waveform typically referred to as the P-wave, the ST segment and the T-wave.

A processor as used herein is a device and/or set of machine-readable instructions for performing tasks. As used herein, a processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example.

Tourniquets (pressure cuffs) 21 in both upper extremities, previously placed on the patient at a preparatory stage, are automatically inflated at the start of the perfusion mode to substantially eighty to a hundred millimeters of mercury, for example. It is noted that both upper extremity tourniquets 21 are connected to the roller pump 7 or controller thereof (e.g., processor 10) and EKG monitor 8, and thus are enslaved to the perfusion/non-perfusion cycles of the system.

(B.) Non-Perfusion Mode (Non-Pumping Period)

In the non-perfusion mode, decompression of the superior vena cava 4 is started. During the non-perfusion mode, the inflatable occlusion balloon 103 collapses, for example, by reverse operation of the roller pump 7 when the two-region catheter 204 is used, or by reverse operation of the fluid pump used with helium, saline or other fluid when the three-region catheter 104 is used. For example, during the non-perfusion mode, the roller pump 7 or fluid pump stops and reverses its rotation for two or three EKG complexes, for example. The reverse operation of the pump will cause the inflatable occlusion balloon 103 to collapse thus allowing the superior vena cava 4 to adequately decompress and drain into the right atrium 5. The collapsed or deflated balloon 103 allows some time for venous decompression through the superior vena cava 4. The upper extremity tourniquets 21 are simultaneously deflated to allow better arterial perfusion and venous decompression of the upper extremities.

During both the perfusion and non-perfusion modes, the catheter may be used to measure the central venous pressure in the superior vena cava, such as through a pressure sensor that communicates with the proximal end of the catheter 104, 204. The periods of the perfusion and non-perfusion modes may be adjusted as needed in response to the measurements of the venous pressure in the superior vena cava.

IV. SECOND EMBODIMENT

Figure 2A:
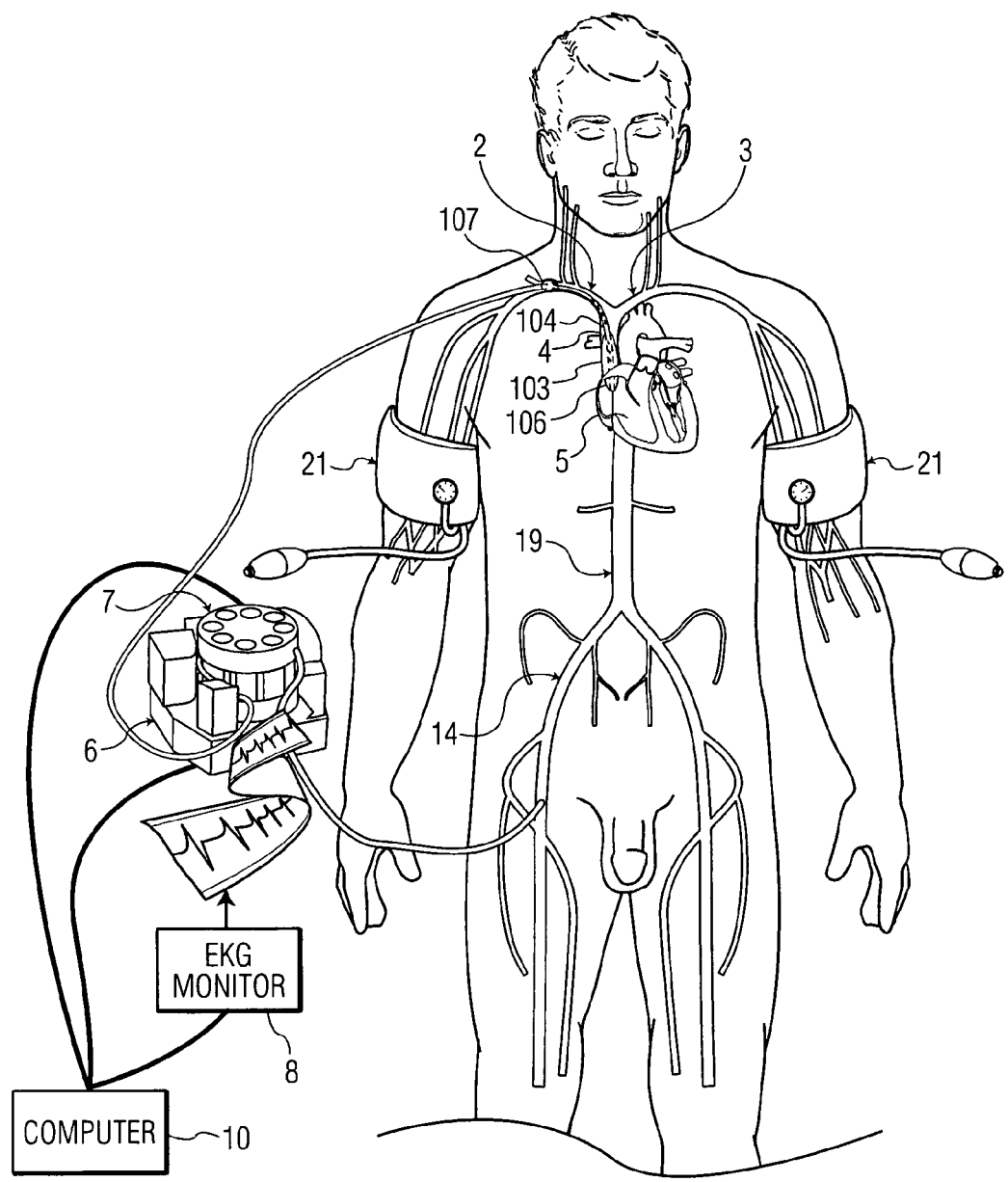
FIG. 2A is an illustration of the system according to another embodiment.
Figure 2B:
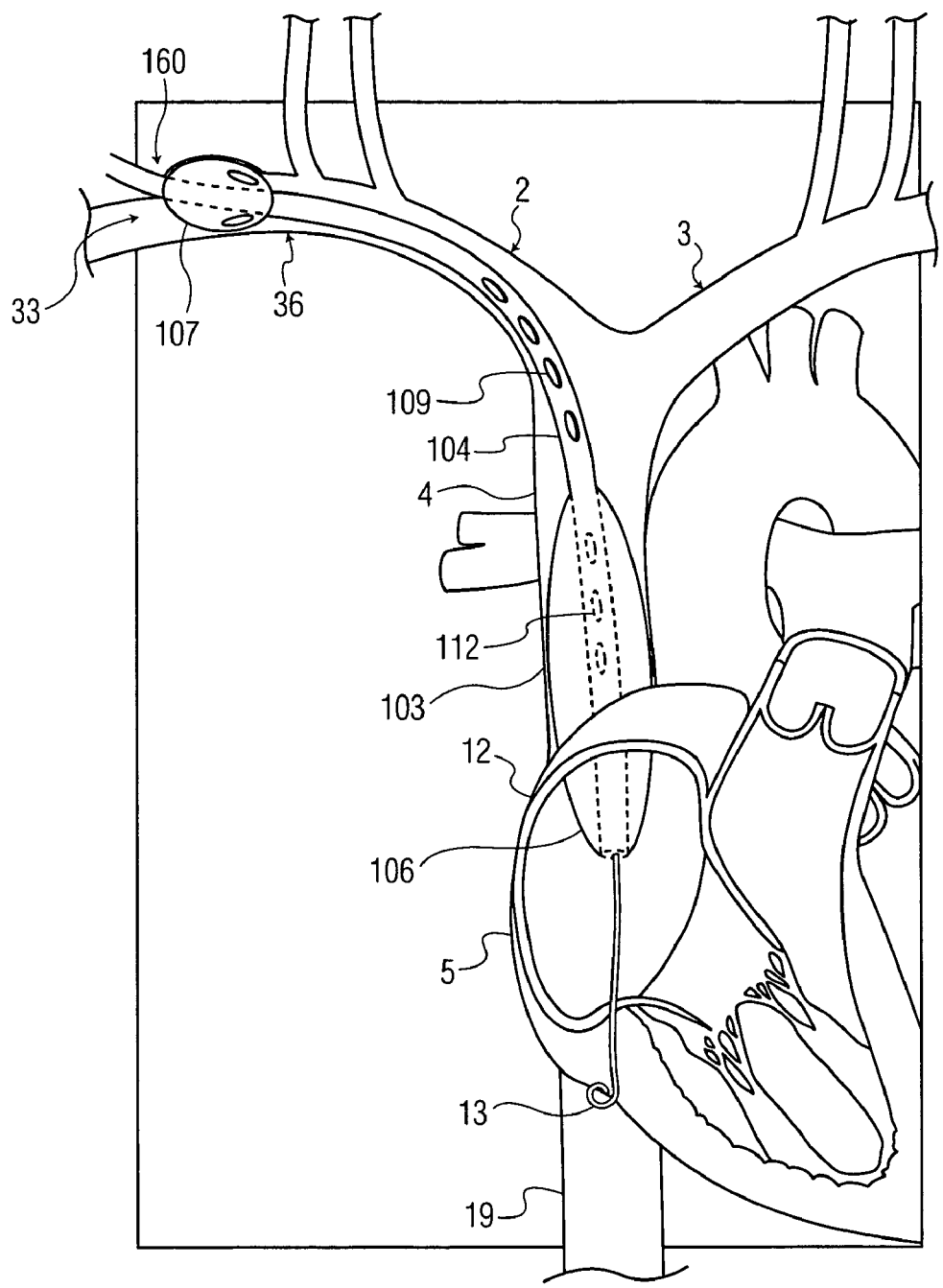
FIG. 2B is a zoom view of the thoracic region of FIG. 2A.

With reference now to FIGS. 2A and 2B of the drawings, there is illustrated a method and system, according to another embodiment for selectively perfusing the brain with retrograde cold blood during acute cessation of perfusion to a specific area of the brain due to closure or lack of flow in the arterial blood supply to that segment.

As illustrated thus far in the previous exemplary embodiment (as shown in FIGS. 1A and 1B), the balloon-tipped catheter 104 includes a single balloon 103. In the present exemplary embodiment (as shown in FIGS. 2A and 2B), an alternative balloon-tipped catheter arrangement is used which includes a pair of balloons 103 and 107. Otherwise, the present embodiment is similar to the previous embodiment in most respects.

In accordance with the present exemplary embodiment illustrated in FIGS. 2A and 2B, the additional short self-inflation balloon 107 is used to occlude the subclavian vein 2 internally. It is noted that the short self-inflation balloon 107 is substantially similar in structure to the balloon 103 described above. For proper operation, the short self-inflation balloon 107 is located close to the insertion site 160 (FIG. 2B) of the subclavian vein 2 and inflates as a result of back-pressure from blood, e.g., during the perfusion mode, to prevent back bleeding through the subclavian vein 2.

V. SHORT SELF INFLATION BALLOON

Alternate Embodiment

Figure 3A:
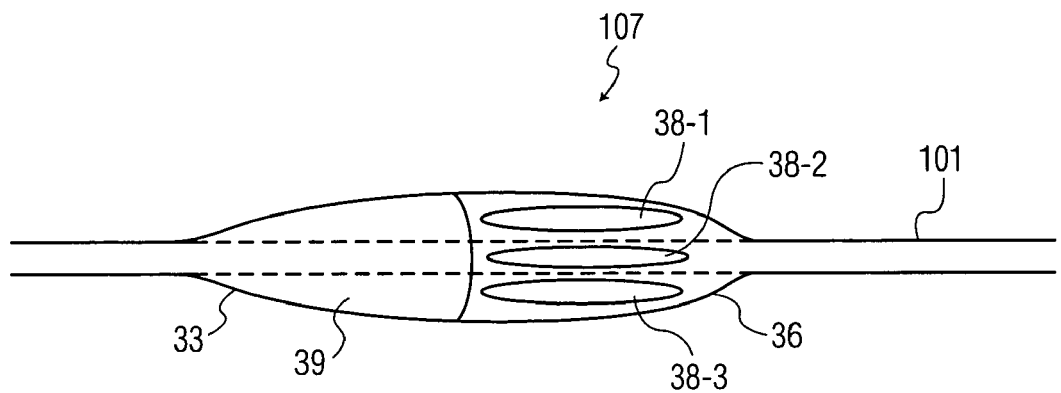
FIGS. 3A-3B illustrate an embodiment of a parachute type balloon for providing occlusion of the insertion site.
Figure 3B:
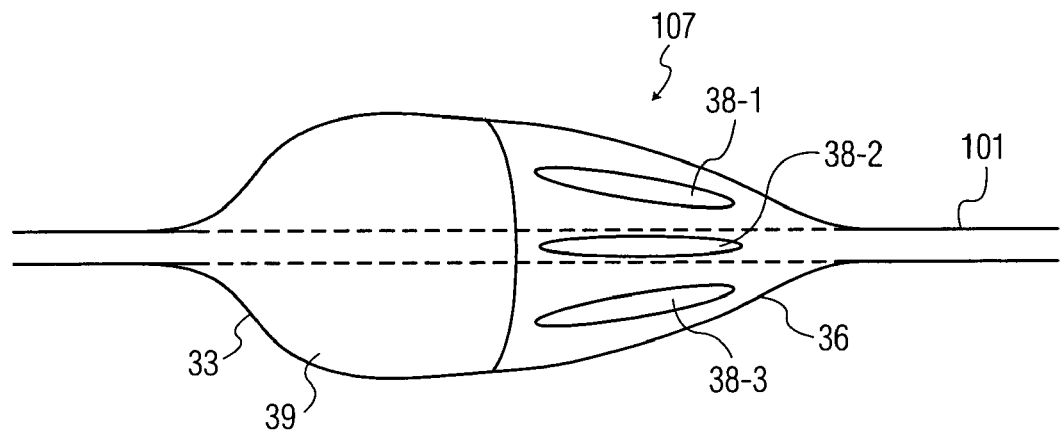

FIGS. 3A and 3B illustrate an alternate embodiment for the short self-inflation balloon 107. The short self-inflation balloon 107 is comprised of two sections in both the deflated and inflated states. A first section (i.e., proximal part) 33 has no openings and a second section (i.e., distal part) 36 has a plurality of openings 38-1, 38-2, 38-3, . . . , 38-n, three of which are shown for ease of explanation. The openings may be elongated and longitudinal for example. The longitudinal openings 38-n allow the arterial blood in the subclavian vein 2 to open the first section (i.e., proximal part) 33 of the balloon like a parachute 39 as shown in FIG. 3B.

In operation, when the system is in the perfusion mode (previously described above), the short self-inflation balloon 107 inflates from the pressure provided from the retrograde blood flow into the longitudinal openings 38-n into the second section (i.e., distal part) 36 part of the balloon 107, where this blood flow is directed from the superior vena cava 4. The blood flow causes the first section (i.e., proximal part) 33 and second section (i.e., distal part) 36 of the balloon 107 to open (inflate) like a parachute as shown in FIG. 3B thereby preventing the relatively high pressure in the subclavian vein 2 from oozing and/or bleeding out of the insertion site 160 (FIG. 2B).

FIGS. 3A-3B show the catheter body 101 of the two-region catheter going through the proximal balloon 107 which surrounds and is sealably attached to a portion of the catheter body 101. However, it should be understood that in the present embodiment, either the two-region or the three-region catheter may be used. Further, the proximal balloon 107 may be of the standard type similar to the distal balloon 103, or the parachute type as described in connection with FIGS. 3A and 3B.

VI. THIRD EMBODIMENT

Femoral Catheter

With reference now to FIGS. 4A & 4B of the drawings, there is illustrated a method and system, according to another embodiment, for selectively perfusing the brain with retrograde cold blood during acute cessation of perfusion to a specific area of the brain due to closure or lack of flow in the arterial blood supply to that segment.

The present embodiment is similar to the previously described embodiments in most respects. However, it is distinguishable from the previously described embodiments in that in the present embodiment, the catheter 104' is significantly longer than the subclavian catheters 104, 204 previously described which in inserted in the subclavian vein 2. The catheter 104', also referred to herein as the femoral catheter 104', is longer than the subclavian catheter 104 to allow for insertion through either right or left femoral vein 15 instead of the right (or left) subclavian vein 2 as described above. The elongated balloon catheter 104' has a length in range from 10 cm to 100 cm and an outer diameter in the range from 1 French to 10 French, or any other desired length and/or diameter. The self-inflation balloon 103 is substantially similar in structure and construction to balloon 103 described above in connection with the previously described embodiments.

It is noted that in the present embodiment, either the two-region or three-region catheter configuration described above may be used. For the three-region catheter configuration, the guide wire region diameter is in the range from 0.2 mm to 5 mm, or any other desired diameter.

The balloon 103 is sized to access and occlude the superior vena cava 4. In particular, the balloon 103 is collapsible to facilitate insertion into and removal from a vessel, and expandable during the perfusion mode to restrict blood flow.

When expanded, the balloon 103 has a maximum periphery that conforms to the inner wall of the vessel, thereby providing a sealed contact between it and the vessel wall. In the perfusion mode, cooled blood from the femoral artery 14 (through cooling device 6 and roller pump 7) is perfused through perfusion holes 109' at the end of the fluid delivery region that extends beyond the inflated balloon 103, thus perfusing the cerebral vasculature retrogradely. It should be noted that in the femoral catheter 104', since it is inserted from the femoral vein 15, the perfusion holes 109' in the fluid delivery region extend beyond the inflated balloon 103, as shown in FIG. 4B. By contrast, the perfusion holes 109 of the subclavian catheter 104 are before the balloon 104 as described in connection with FIGS. 1A, 1B. As is apparent, the perfusion holes 109, 109' of both the subclavian and femoral catheters 104, 104' are configured to perfuse the cerebral vasculature retrogradely.

VII. FOURTH EMBODIMENT

Extended Femoral Catheter

FIGS. 5A & 5B illustrates another embodiment similar to the above embodiment described in connection with FIGS. 4A & 4B. In this embodiment, the balloon 103 is constructed to be of a sufficient length to simultaneously occlude both the superior vena cava 4 and inferior vena cava 19. The present embodiment is identical with the previous embodiment in all other respects.

It should be noted that there is some clinical evidence that occlusion of the inferior vena cava 19 during circulatory arrest in addition to occlusion of the superior vena cava 19, increases the de-saturated blood coming back from the carotid arteries thus providing further protection to the brain. Of course if desired, a longer balloon 103 to simultaneously occlude both the superior vena cava 4 and inferior vena cava 19 may be used with any of the embodiments described herein. It is noted that in the present embodiment, as in the other embodiments, either the two-region or three-region catheter configuration may be used. It should be further noted that, if desired, the femoral catheter 104' may have a second balloon similar to the one described in connection with FIGS. 2A, 2B, 3, positioned near the insertion site to prevent back bleeding. The second balloon may be of the normal type or the parachute type shown in FIG. 107. However typically there is no need to use such a second balloon with the femoral catheter 104', since typically no back-bleeding occurs due to the lower back-pressure at the femoral vein's insertion site during the perfusion mode as compared to the back-pressure at the subclavian vein's insertion site.

VIII. FIFTH EMBODIMENT

Two Catheter Embodiment

FIG. 6 illustrates another embodiment. In this embodiment, two catheters are utilized. The first catheter 602, referred to hereafter as the femoral vein catheter 602 and a second catheter, referred to hereafter as the subclavian vein perfusion catheter 630. The femoral vein catheter 602 is of a sufficient length to allow for insertion through the groin (e.g., right or left femoral vein) and is advanced through the femoral vein 15 (FIGS. 4, 5) using the guide wire 13 through the right atrium 5 such that, upon correct positioning, the balloon member 604 is positioned substantially in the superior vena cava 4 with the tip 608 of the femoral vein catheter 602 placed at very close proximity to the right atrial-superior vena cava junction 12 substantially proximal to the take-off of the left inominate vein 3. Similar to the embodiments described above in connection with the two-region catheter, the balloon 604 is inflated in the perfusion mode by pumping fluid via a fluid pump into the inflation region 641. The fluid enters the balloon through inflation holes 612 for inflation. Reverse operation of the fluid pump deflates the balloon.

The second catheter 630 is inserted through the subclavian vein 2 using, for example, a guide wire as previously described, and does not have a balloon affixed to it. The purpose of the subclavian vein catheter 630 is to take blood away from the femoral artery 14, pass it through cooling device 6 and roller pump 7 as described above such as in connection with FIG. 1, and use the cooled blood to perfuse through the holes 609 to the brain retrogradely through its venous circulation while the femoral vein catheter 602 is occluding the superior vena cava 4.

IX. SIXTH EMBODIMENT

Two Catheter Embodiment Including Short Self Inflation Balloon

In an alternate embodiment, the subclavian vein catheter 630 includes a short self-inflation balloon similar to the balloon 107 shown in FIGS. 2A-2B, to prevent back bleeding through the subclavian vein 2 at the insertion site of the subclavian vein catheter 630 in the subclavian vein 2. The short self-inflation balloon may be a standard type as described in connection with FIGS. 1B, 2B, or a parachute type as described above with respect to FIG. 3. Of course if desired, the balloon 107 may also be used to occlude any insertion site such as at the subclavian or femoral vein so as to prevent back bleeding.

Although this invention has been described with reference to particular embodiments, it will be appreciated that many variations will be resorted to without departing from the spirit and scope of this invention as set forth in the appended claims. The specification and drawings are accordingly to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) every "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise; and h) no specific sequence of acts is intended to be required unless specifically indicated.

The invention claimed is:

1. A method of perfusing an oxygenated medium into a cerebral venous system of a living human, said living human comprising a right subclavian vein, a superior vena cava, a femoral artery, a heart, a first upper extremity, and a second upper extremity, the method comprising:

providing a catheter system, said catheter system comprising:
- a proximal section comprising a parachute valve balloon, said parachute valve balloon comprising a first, proximal section with no openings and a second, distal section with a plurality of openings,
- a mid-section comprising a length of catheter containing perfusion holes, and
- a distal section comprising an occlusive balloon;

inserting the catheter system percutaneously through an entry site in said right subclavian vein and into said superior vena cava so that said occlusive balloon is positioned in said superior vena cava, and so that said parachute valve balloon is positioned in said right subclavian vein at a position allowing occlusion of flow of said oxygenated medium to said first upper extremity while also allowing said oxygenated medium flow to said cerebral venous system;

occluding said superior vena cava with said occlusive balloon during a first length of time;

preventing flow of said oxygenated medium into said second upper extremity of said living human during said first length of time;

providing said oxygenated medium from said femoral artery of said living human;

flowing said oxygenated medium through said catheter system, out of said perfusion holes, and into said cerebral venous system at a location proximal to and upstream of said occlusive balloon during said first length of time such that said oxygenated medium moves in a retrograde direction to perfuse said cerebral venous system;

occluding said right subclavian vein with said parachute valve balloon during said first length of time in response to pressure from said oxygenated medium moving retrograde into said plurality of openings in said second, distal section of said parachute valve balloon, thereby preventing oozing of said oxygenated medium out of said right subclavian vein through said entry site and preventing flow of said oxygenated medium into said first upper extremity of said living human; and conducting each aforesaid action during beating of said heart of said living human.

2. The method of claim 1, further comprising:
discontinuing occlusion of said superior vena cava for a second length of time; and
allowing blood flow in an antegrade direction through said superior vena cava.

3. The method of claim 1, wherein occluding said superior vena cava during said first length of time comprises inflating said occlusive balloon disposed on said catheter system distal section.

4. The method of claim 1, wherein preventing flow of said oxygenated medium into said second upper extremity further comprises restricting said second upper extremity with one of a pressure cuff and a parachute valve balloon.

5. The method of claim 1, wherein flowing said oxygenated medium in a retrograde direction comprises utilizing a roller pump to remove oxygen rich blood from said femoral artery in said living human and introduce said oxygen rich blood into said cerebral venous system, optionally in combination with cooling said oxygen rich blood.

6. The method of claim 1, further comprising:
removing occlusion of said superior vena cava after said first length of time; and
allowing drainage of blood from said first upper extremity and said second upper extremity after said first length of time.

7. The method of claim 1, further comprising:
cooling said oxygenated medium prior to providing said oxygenated medium.

* * * * *